(12) United States Patent
Nevo et al.

(10) Patent No.: US 10,321,870 B2
(45) Date of Patent: Jun. 18, 2019

(54) METHOD AND SYSTEM FOR BEHAVIORAL MONITORING

(71) Applicant: Ramot at Tel-Aviv University Ltd., Tel-Aviv (IL)

(72) Inventors: Uri Nevo, Tel-Aviv (IL); Keren Zeevy Sela, Tel-Aviv (IL); Asaf Liberman, Tel-Aviv (IL); Dana Erlich, Tel-Aviv (IL); Adam Harel, Tel-Aviv (IL); Jonathan Marton, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 14/700,277

(22) Filed: Apr. 30, 2015

(65) Prior Publication Data

US 2015/0313529 A1 Nov. 5, 2015

Related U.S. Application Data

(60) Provisional application No. 61/986,918, filed on May 1, 2014.

(51) Int. Cl.
*A61B 5/00* (2006.01)
*A61B 5/16* (2006.01)
(Continued)

(52) U.S. Cl.
CPC .......... *A61B 5/4809* (2013.01); *A61B 5/1112* (2013.01); *A61B 5/1118* (2013.01); *A61B 5/165* (2013.01); *A61B 5/22* (2013.01); *A61B 5/225* (2013.01); *A61B 5/4803* (2013.01); *A61B 5/6898* (2013.01); *A61B 5/7264* (2013.01);
(Continued)

(58) Field of Classification Search
CPC ..... A61B 5/1112; A61B 5/1118; A61B 5/165; A61B 5/4803; A61B 5/4809; A61B 5/4812; A61B 5/4815; A61B 5/6898; A61B 5/7264; A61B 5/7275; A61B 2560/0204; A61B 2560/0209; G06F 19/3418; H04W 4/025; H04W 4/027; H04W 4/028
See application file for complete search history.

(56) References Cited

U.S. PATENT DOCUMENTS 6,591,238 B1 * 7/2003 Silverman ............... G10L 17/26
704/270
8,181,113 B2 5/2012 Abbott et al.
(Continued)

FOREIGN PATENT DOCUMENTS

CA 2836431 A1 * 6/2015 ............. A47C 31/00

OTHER PUBLICATIONS

Campbell et al. "From Smart to Cognitive Phones", Pervasive Computing, IEEE CS, p. 7-11, Jul.-Sep. 2012.
(Continued)

*Primary Examiner* — Devin B Henson

(57) ABSTRACT

A method of analysis is disclosed. The method comprises: receiving from a mobile device of a subject sensor data and/or device state data, analyzing the data to provide at least one behavioral pattern associated with the subject, comparing the behavioral pattern with a reference behavioral pattern, and estimating the likelihood that the subject is experiencing or is expected to experience an abnormal condition based on the comparison.

23 Claims, 6 Drawing Sheets
(3 of 6 Drawing Sheet(s) Filed in Color)

(51) Int. Cl.
*A61B 5/11* (2006.01)
*A61B 5/22* (2006.01)

(52) U.S. Cl.
CPC .......... *A61B 5/7275* (2013.01); *A61B 5/4812* (2013.01); *A61B 5/4815* (2013.01)

(56) References Cited

U.S. PATENT DOCUMENTS

| | | | |
|---|---|---|---|
| 8,719,188 B2 | 5/2014 | Kuhn et al. | |
| 8,810,430 B2 | 8/2014 | Proud | |
| 8,892,461 B2 | 11/2014 | Lau et al. | |
| 8,914,018 B2 | 12/2014 | Tatman et al. | |
| 2011/0245633 A1* | 10/2011 | Goldberg | A61B 5/681 600/301 |
| 2012/0083668 A1* | 4/2012 | Pradeep | A61B 5/04015 600/300 |
| 2012/0290266 A1* | 11/2012 | Jain | G06F 19/3406 702/187 |
| 2012/0326873 A1* | 12/2012 | Utter, II | G06F 3/016 340/573.1 |
| 2013/0018284 A1* | 1/2013 | Kahn | G04G 13/026 600/595 |
| 2013/0345524 A1* | 12/2013 | Meyer | G06F 19/363 600/301 |
| 2014/0052475 A1 | 2/2014 | Madan et al. | |
| 2014/0100835 A1 | 4/2014 | Majumdar et al. | |
| 2014/0288876 A1* | 9/2014 | Donaldson | A61B 5/1118 702/141 |
| 2014/0358473 A1* | 12/2014 | Goel | A61B 5/1118 702/141 |
| 2015/0148621 A1* | 5/2015 | Sier | A61B 5/7267 600/301 |
| 2015/0164238 A1* | 6/2015 | Benson | G16H 50/30 340/540 |
| 2015/0179079 A1* | 6/2015 | Rodriguez, Jr. | G09B 5/00 434/236 |

OTHER PUBLICATIONS

Google "Be Well", BeWell Team, Health & Fitness, Android Apps on Google Play, Jul. 4, 2012.
Google "T2 Mood Tracker", Health & Fitness, Android Apps on Google Play, May 7, 2013.
IMedicalApps Team "Mobilyze—A Therapist in Your Pocket [#Med2]", iMedical Apps LLC, May 10, 2012.
Jackson "Depression App Claims to Give Patients a Lift", FierceMobile Healthcare Weekly Newsletter, Jun. 4, 2012, FierceMarkets, a Division of Questex Media Group LLC, 2014.
LiKamWa et al. "MoodScope: Building a Mood Sensor From Smartphone Usage Patterns", Proceedings of the 11th Annual International Conference on Mobile systems, Applications, and Services, MobiSys '13, Taipei, Taiwan, Jun. 25-28, 2013, p. 389-402, 2013.
Limer "Mobilyze! App Aims Use Your Smartphone to Diagnosis Depression, Dole Out Advice", Geekosystem, Feb. 10, 2012.
Northcube AB "Sleep Cycle Alarm Clock", Northcube AB, iTunes Preview, Health & Fitness, Version 4.4.1, Jan. 9, 2014.
Pentland et al. "Using Reality Mining to Improve Public Health and Medicine", Robert Wood Johnson Foundation, Whitepaper, 16 P., Feb. 2009.
Steele "Smartphone App for Bipolar Patients Wins $100K Prize", Jul. 3, 2013, Cornell Chronicle, 2 P., Apr. 22, 2014.

* cited by examiner

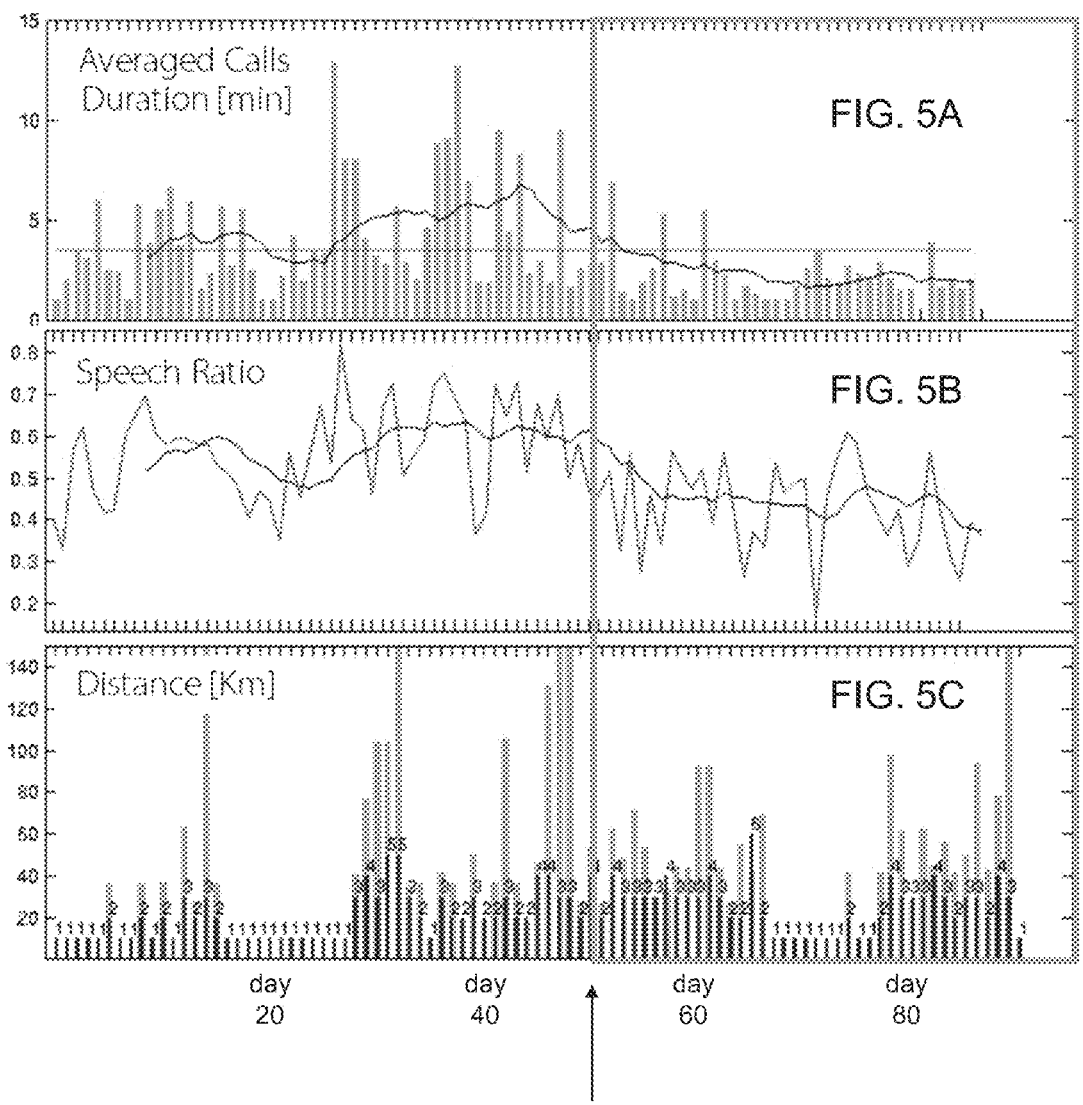

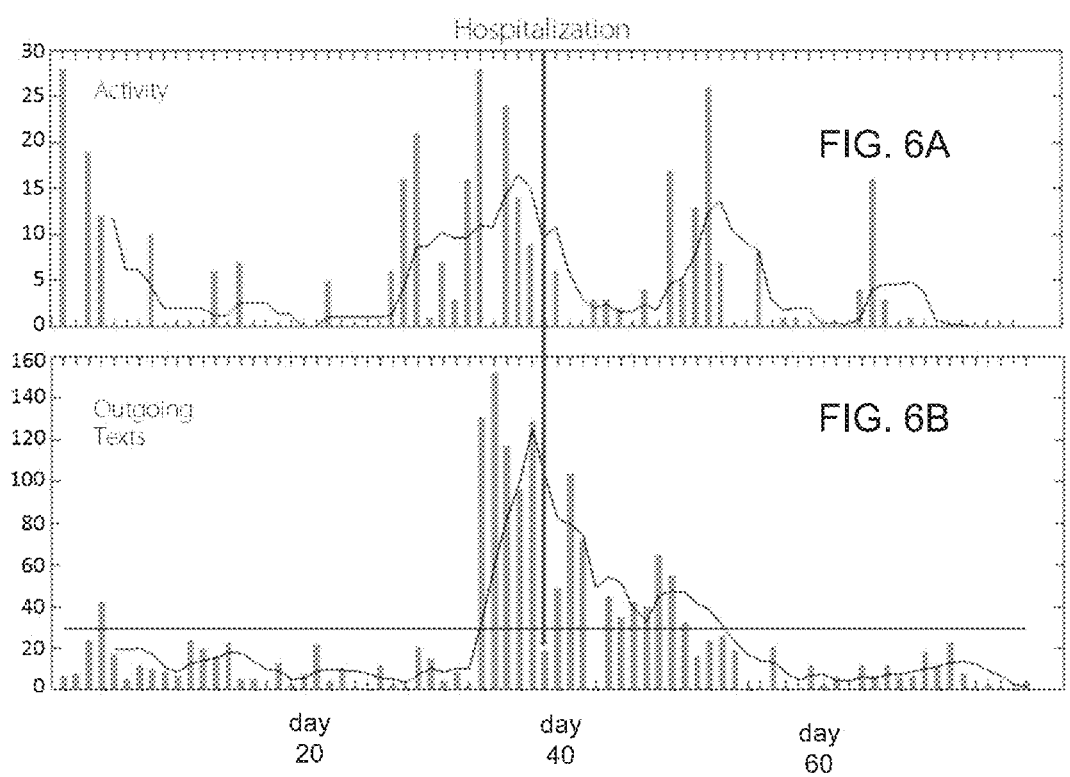

000# METHOD AND SYSTEM FOR BEHAVIORAL MONITORING

RELATED APPLICATION

This application claims the benefit of priority under 35 USC 119(e) of U.S. Provisional Patent Application No. 61/986,918 filed on May 1, 2014, the contents of which are incorporated herein by reference in their entirety.

FIELD AND BACKGROUND OF THE INVENTION

The present invention, in some embodiments thereof, relates to monitoring and, more particularly, but not exclusively, to a method and system for behavioral monitoring.

Systems that employ cellular phones for monitoring subjects are known and found, for example, in U.S. Pat. No. 8,181,113; U.S. Patent Application Publication No. 20140052475; Campbell et al., 2012, "From Smart to Cognitive Phones," IEEE pervasive computing; Pentland et al., 2009, "Using Reality Mining to Improve Public Health and Medicine," A Whitepaper Commissioned by the Robert Wood Johnson Foundation; and LiKamWa et al., 2013, "MoodScope: Building a Mood Sensor from Smartphone Usage Patterns," in MobiSys 2013, The 11th International Conference on Mobile Systems, Applications, and Services, Taipei, Taiwan.

For example, U.S. Pat. No. 8,181,113 discloses a software facility that exchanges information between sources of context data and consumers of context data. A characterization module operating in a wearable computer system receives context information from one or more context servers, and provides that information to one or more context clients. The context information represents a context of the wearable, the user of the wearable, the surrounding physical environment and/or the available electronic data environment. Attributes are used for modeling aspects of the context.

U.S. Patent Application Publication No. 20140052475 discloses a method for supporting a subject through a treatment regimen. A log of use of a native communication application executing on a mobile computing device by the subject within a time period is accessed, and a survey response corresponding to the time period is received from the subject. An adherence to the treatment regimen by the subject within the time period is estimated based on the survey response. The log is correlated with the adherence to the treatment regimen. The process is repeated and a subject regimen adherence model comprising the logs of use of the native communication application and the adherences is generated. A third log of use of the native communication application is accessed and the adherence to the treatment regimen is estimated based on the subject regimen adherence model and the third log.

Campbell et al. disclose a mobile health app that can automatically monitor and promote multiple aspects of physical and emotional well-being. The app continuously tracks user behaviors along three distinct health dimensions without requiring user input. Classification algorithms run directly on the phone to automatically infer the user's estimated sleep duration, physical activity, and social interaction.

SUMMARY OF THE INVENTION

According to an aspect of some embodiments of the present invention there is provided a method of analysis, comprising: receiving from a mobile device of a subject sensor data and/or device state data; analyzing the data to provide at least one behavioral pattern associated with the subject; comparing the behavioral pattern with a reference behavioral pattern; and estimating the likelihood that the subject is experiencing or is expected to experience an abnormal condition based on the comparison.

According to some embodiments of the invention the mobile device comprises a touch screen, and the analysis comprises determining pressure applied by the subject to the touch screen.

According to some embodiments of the invention the method comprises remotely controlling the mobile device so as to vary a sampling rate of sensors of the mobile device.

According to some embodiments of the invention the analysis comprises determining level of physical activeness of the subject.

According to some embodiments of the invention the determination of the level of activeness comprises measuring speed of movement of the subject.

According to some embodiments of the invention the determining the level of activeness comprises identifying periodic movements of the subject, based on the location data and/or the acceleration data.

According to some embodiments of the invention the sensor data comprise audio data, and wherein the analysis comprises identifying speech compression in the audio data.

According to some embodiments of the invention the analysis comprises estimating sleep onset time according to a local clock.

According to some embodiments of the invention the analysis comprises estimating sleep duration.

According to some embodiments of the invention the analysis comprises identifying temporary awakening periods.

According to some embodiments of the invention the analysis comprises calculating a score pertaining to activity level of the subject over at least one communication network.

According to some embodiments of the invention the analysis comprises executing a voice analysis procedure.

According to some embodiments of the invention the voice analysis procedure is executed to identify speech compression event.

According to some embodiments of the invention the sensor data comprise at least two different types of data.

According to some embodiments of the invention the sensor data comprise at least three different types of data.

According to some embodiments of the invention the sensor data comprise at least four different types of data.

According to some embodiments of the invention the sensor data comprise data selected from the group consisting of location data, acceleration data, orientation data, audio data, ambient illumination data.

According to some embodiments of the invention the device state data comprise data selected from the group consisting of at least one of electronic communication log data and screen state data.

According to some embodiments of the invention the analysis comprises executing a machine learning procedure.

According to some embodiments of the invention the machine learning procedure comprises a supervised learning procedure.

According to some embodiments of the invention the machine learning procedure comprises at least one procedure selected from the group consisting of clustering, support vector machine, linear modeling, k-nearest neighbors' analysis, decision tree learning, ensemble learning procedure, neural networks, probabilistic model, graphical model, Bayesian network, and association rule learning.

According to some embodiments of the present invention the method transmits a physician (e.g., a psychiatric physician) an alert when a deviation from a predefined behavioral pattern is observed. According to some embodiments of the present invention the behavioral pattern is obtained from a plurality of numerical behavioral parameters and the method transmits a physician (e.g., a psychiatric physician) an alert when the value of one or more of the numerical behavioral parameters exceeds a predetermined threshold.

According to some embodiments of the present invention there is provided a method of treating a subject, the method comprising monitoring a plurality of behavioral parameters of the subject, analyzing the parameters to obtain a behavioral pattern, and treating the subject based on the behavioral pattern. In some embodiments of the present invention the treatment is a medical treatment, and the method adjusts the medical treatment responsively to a change in the behavioral pattern.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart diagram of a method suitable for analysis of a subject according to various exemplary embodiments of the present invention;

FIG. 2 is a schematic illustration of a data processing system according to some embodiments of the present invention;

FIG. 3 is a schematic illustration showing an overview of a deployed system which can be used according to some embodiments of the present invention;

FIG. 4 is a sonogram obtained according to some embodiments of the present invention;

Figure 1:
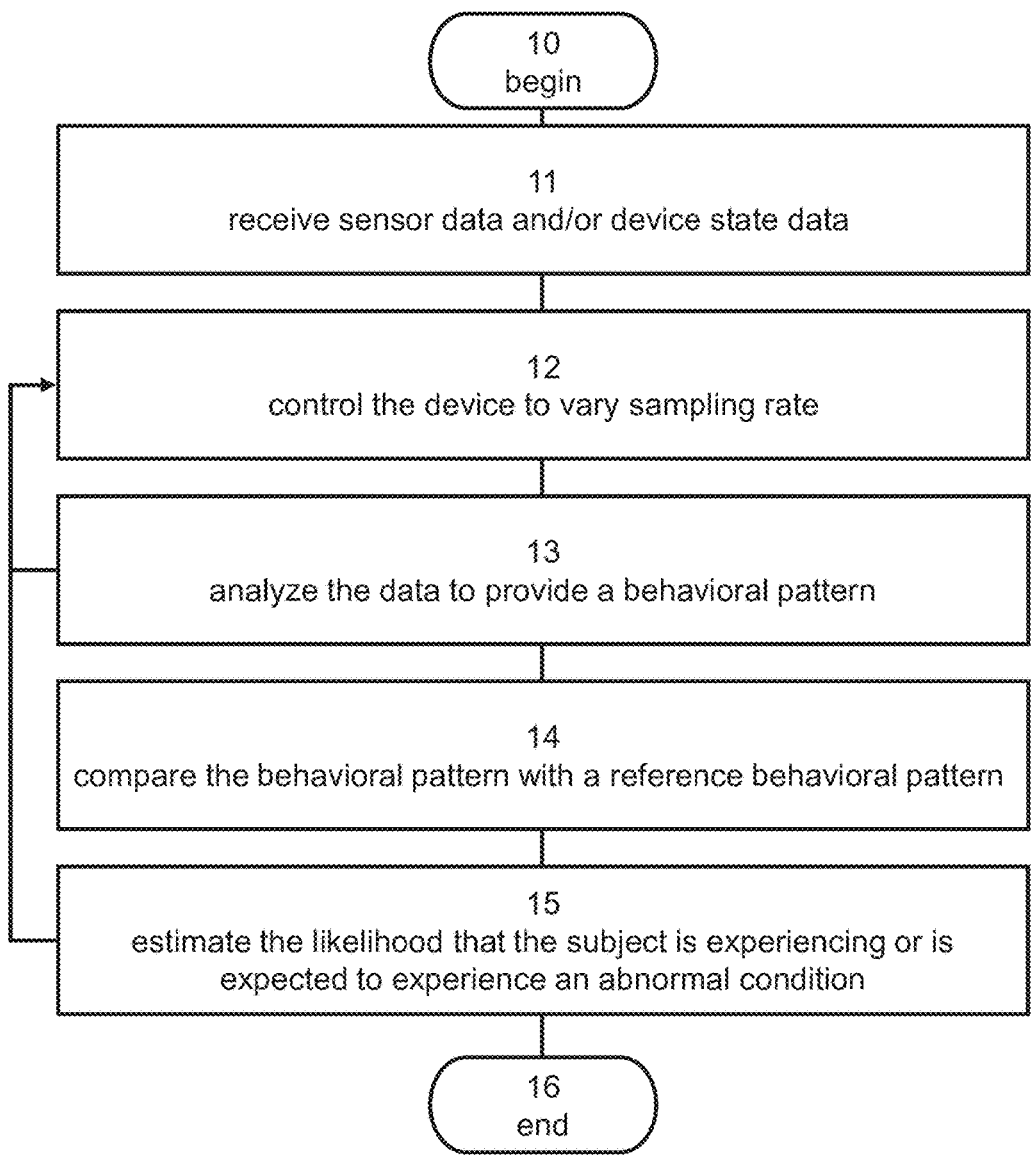

FIGS. 5A-C show averaged call duration, speech ratio and motion distance, respectively, of a unipolar subject, as measured during experiments performed according to some embodiments of the present invention; and FIGS. 6A-B show an activity parameter and No. of outgoing text messages, respectively, of a bipolar subject, as measured during experiments performed according to some embodiments of the present invention.

DESCRIPTION OF SPECIFIC EMBODIMENTS OF THE INVENTION

The present invention, in some embodiments thereof, relates to monitoring and, more particularly, but not exclusively, to a method and system for behavioral monitoring.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors found that sensor data and/or device state data received from a mobile device of a subject can be used for behavioral monitoring. Such monitoring can be used, for example, to facilitate preventive medicine, wherein type and extent of a treatment can be adjusted based on the monitored behavior.

FIG. 1 is a flowchart diagram of a method suitable for analysis of a subject according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

Computer programs implementing the method of the present embodiments can commonly be distributed to users on a distribution medium such as, but not limited to, a floppy disk, CD-ROM, flash drives or the like. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method can be embodied in many forms. For example, it can be embodied in on a tangible medium such as a computer for performing the method operations. It can be embodied on a computer readable medium, comprising computer readable instructions for carrying out the method operations. In can also be embodied in electronic device having digital computer capabilities arranged to run the computer program on the tangible medium or execute the instruction on a computer readable medium.

Referring to FIG. 1, the method begins at 10 and optionally and preferably continues to 11 at which sensor data and/or device state data are received from a mobile device of the subject. The mobile device can be any of a variety of computing devices, including, without limitation, a cell phone, a smartphone, a handheld computer, a laptop computer, a notebook computer, a tablet device, a notebook, a media player, a Personal Digital Assistant (PDA), a camera, a video camera and the like. In various exemplary embodiments of the invention the mobile device is a smart phone.

The sensor data can be received from any of the sensors of the mobile device. Representative examples of sensor data that can be received at 11 include, without limitation, accelerometeric data, gravitational data, gyroscopic data, compass data, GPS geolocation data, proximity data, illumination data, audio data, video data, temperature data, geomagnetic field data, orientation data and humidity data.

The device state data can describe the state of the device or any component thereof. Representative examples of device state data that can be received include, without limitation, electronic communication log data, screen state data, power on/off data, battery state data, and the like.

The collection of data at 11 is typically, but not necessarily at a predetermined sampling rate, such as, but not limited to, from one to a few times per day, to one to a few times per hour. In various exemplary embodiments of the invention, the method remotely controls 12 the mobile device of the subject so as to vary the sampling rate of the sensors. In these embodiments the sampling rate is increased or decreased based on one or more criteria. For example, when the method identifies a reduced activity of the subject (for example, when the subject is a sleep) the sampling rate can be decreased, and when the method identifies an increase in the activity of the subject (for example, high volume of text messages transmitted, rapid movement, etc) the sampling rate can be increased. The sampling rate can also be changed prior to, during or subsequent to particular activities of the subject. For example, before going to sleep, during sleep walk and while moving, the sampling rate can be increased. The sampling rate can also be set based on a subject-specific protocol. For example, when a physician requests a higher sampling rate, e.g., when deviation from normal behavioral patterns is suspected, the method can control the sensors to provide a higher sampling rate.

The fulfillment of one or more of the above criteria and protocols can be determined by analyzing the data. Thus, according to various exemplary embodiments of the present invention the method proceeds to 13 at which the received data are analyzed to provide at least one behavioral pattern associated with the subject. This is optionally and preferably done by estimating one or more, more preferably multiple of, behavioral parameters. The entire set of behavioral parameters for a particular subject over a predetermined period of time (e.g., from 1 hour to one day) is referred to herein as metadata. Representative examples of behavioral parameters that can be estimated include, without limitation, tone of voice, amplitude of voice, variations in amplitude and pitch, speech compression, motion acceleration, motion velocity, motion frequency, amount and type of periodic movements, acceleration in periodic movements, volume of activity in communication applications, volume of use of internet, use of internet for specific and predetermined content, duration of exposure to light during night time, amount of ambient illumination and the like. Preferably, the behavioral parameters are quantified, namely they are expressed numerically.

Another behavioral parameter that is contemplated is the pressure applied by the subject to a touch screen of the device. The pressure can be obtained by measuring the area of the screen that was touched and/or by measuring the activity sensors.

An additional behavioral parameter that is contemplated is the level of physical activeness of the subject. Such level of activeness can be determined, for example, by measuring the speed of movement of the subject, and/or by identifying periodic movements of the subject, based on location and/or acceleration data.

The present embodiments also contemplate audio related behavioral parameters that are estimated from audio date received from an audio sensor of the device. A representative example of such a parameter is speech compression (also known in the literature as pressured speech), wherein the method identifies rapid and/or frenzied patterns in the subject's voice. Such identification can be done by a computer executing a voice analysis procedure, such as, but not limited to, the procedure disclosed in U.S. Pat. No. 6,591,238 the contents of which are hereby incorporated by reference.

The present embodiments also contemplate sleep related behavioral parameters that are estimated from motion sensors and/or device state data (e.g., screen state data and log data). One such sleep related behavioral parameter is the estimated duration of sleep, that is typically measured from the time of the first sleep onset during a sleep session to the time of last sleep awakening during the same sleep session. Another sleep related behavioral parameter is an estimated sleep offset that is calculated based on a local clock at the time zone at which the subject is present. The estimated sleep offset is typically expressed in units of time measuring the time difference between the beginnings of two (e.g., two consecutive) sleep sessions. The time difference can be modulo 24, so that for example, when one sleep session begins at 01:00 and another sleep session begins at 02:00 of the following day, the estimated sleep offset can be set to +1 hour. Another sleep related behavioral parameter is estimated sleep activity which is a measure of the restlessness of the subject during sleep. Typically, the estimated sleep activity can be obtained by monitoring motion and temporary awakening events during a sleep session.

In some embodiments of the invention the method determines whether or not the subject is sleeping based on information from a combination of sensors including, without limitation, battery charge state of the mobile device, screen activity of the mobile device, power state of the mobile device (on or off), ambient light condition, communication (voice, SMS and internet), activity sensors and/or location sensors.

Each estimated behavior parameter forms an estimated point in a multidimensional behavioral space. The behavior parameters are optionally and preferably tracked, continuously or intermittently, over time to provide a collection of points, each representing the estimated behavior at one time-interval. In various exemplary embodiments of the invention the collection of points over a predetermined time period (e.g., over one day) are analyzed so as to classify the points in the multidimensional space into one or more classification groups, each defining a behavioral pattern of the subject. The classification optionally and preferably includes clustering. The analysis can optionally and preferably include use of a machine learning procedure.

As used herein "behavioral pattern" refers to a set of two or more values, wherein each value is calculated based on one or more different behavioral parameter, and wherein at least one or at least two or at least three or at least four or at least five, e.g., each of the behavioral parameters is selected from the above list of behavioral parameters.

Thus, a behavioral pattern P can be defined as the set of values { P1, P2, P3} where P1 is calculated based on behavioral parameters A and B, P2 is calculated based on behavioral parameter C, and P3 is calculated based on behavioral parameters A and D. This example is not to be considered as limiting and it is to be understood that a pattern can include any number of values (preferably two or more).

When two or more behavioral patterns are estimated for a particular subject over a particular period of time, the two or more behavioral patterns optionally and preferably differ from each other by the types of behavioral parameters that are used to calculate at least one of the values that form the set.

The same behavioral pattern can be defined for a particular subject more than once, each time over a different period of time, but using the same behavioral parameter. Thus, for example, for a particular subject, behavioral pattern P(T1) can be defined as the set of values {P1(T1), P2(T1), P3(T1)} over one time period T1 (e.g., a particular day), and behavioral pattern P(T2) can be defined as the set of values {P1(T2), P2(T2), P3(T2)} over another time period T2 (e.g., the following day), where both P1(T1) and P1(T2) are calculated based on the same behavioral parameters, where both P2(T1) and P2(T2) are calculated based on the same behavioral parameters, and both P3(T1) and P3(T2) are calculated based on the same behavioral parameters.

One example of a behavioral pattern is a sleep pattern. The sleep pattern can be calculated based of data from one of the motion sensors and/or device state data (e.g., screen state data and log data). The sleep pattern optionally and preferably indicates sleeping habits, and may be defined as a set of values respectively corresponding to the estimated duration of sleep, the estimated sleep offset, and the estimated sleep activity.

Another example of a behavioral pattern is a social interaction pattern. The social interaction pattern optionally and preferably indicates interaction habits, and may be defined as a set of values respectively corresponding to physical social interaction, vocal social interaction, and virtual social interaction. The physical social interaction can be calculated based of data from sensors that relate to location and motion of the subject, the vocal social interaction can be calculated based on sensors that relate to audio features, and/or the virtual social interaction can be calculated based on log data that relate to use of messaging applications, including text messaging, image messaging, emails, and internet based messaging.

The analysis at 13 optionally and preferably comprises executing a machine learning procedure. The machine learning procedure can be a supervised, an unsupervised or reinforcement learning procedure.

Supervised learning is typically applied to labeled data, for example, in the form of a set of pairs (x, y), and the aim is to find a function fin an allowed class of functions that matches the pairs. Unsupervised learning is typically applied to unlabeled data wherein the procedure searches for hidden structure in the data. In reinforcement learning, the data is generated by interactions with the environment, wherein an action applied to the environment to generate an observation and an instantaneous reward. The aim in reinforcement learning is to discover a policy for selecting actions that maximize some measure of a long-term reward.

Representative examples of machine learning procedures suitable for the present embodiments include, without limitation, clustering, support vector machine, linear modeling, k-nearest neighbors analysis, decision tree learning, ensemble learning procedure, neural networks, probabilistic model, graphical model, Bayesian network, and association rule learning. Following is an overview of some machine learning procedures suitable for the present embodiments.

Association rule algorithm is a technique for extracting meaningful association patterns among features.

The term "association", in the context of machine learning, refers to any interrelation among features, not just ones that predict a particular class or numeric value. Association includes, but it is not limited to, finding association rules, finding patterns, performing feature evaluation, performing feature subset selection, developing predictive models, and understanding interactions between features.

The term "association rules" refers to elements that co-occur frequently within the databases. It includes, but is not limited to association patterns, discriminative patterns, frequent patterns, closed patterns, and colossal patterns.

A usual primary step of association rule algorithm is to find a set of items or features that are most frequent among all the observations. Once the list is obtained, rules can be extracted from them.

Self-organizing map is an unsupervised learning technique often used for visualization and analysis of high-dimensional data. Typical applications are focused on the visualization of the central dependencies within the data on the map. The map generated by the algorithm can be used to speed up the identification of association rules by other algorithms. The algorithm typically includes a grid of processing units, referred to as "neurons". Each neuron is associated with a feature vector referred to as observation. The map attempts to represent all the available observations with optimal accuracy using a restricted set of models. At the same time the models become ordered on the grid so that similar models are close to each other and dissimilar models far from each other. This procedure enables the identification as well as the visualization of dependencies or associations between the features in the data.

Feature evaluation algorithms are directed to the ranking of features or to the ranking followed by the selection of features based on their impact on the response of the subject under analysis to the selected food.

The term "feature" in the context of machine learning refers to one or more raw input variables, to one or more processed variables, or to one or more mathematical combinations of other variables, including raw variables and processed variables. Features may be continuous or discrete.

Information gain is one of the machine learning methods suitable for feature evaluation. The definition of information gain requires the definition of entropy, which is a measure of impurity in a collection of training instances. The reduction in entropy of the target feature that occurs by knowing the values of a certain feature is called information gain. Information gain may be used as a parameter to determine the effectiveness of a feature in explaining the response of the subject under analysis to the selected food. Symmetrical uncertainty is an algorithm that can be used by a feature selection algorithm, according to some embodiments of the present invention. Symmetrical uncertainty compensates for information gain's bias towards features with more values by normalizing features to a [0, 1] range.

Subset selection algorithms rely on a combination of an evaluation algorithm and a search algorithm. Similarly to feature evaluation algorithms, subset selection algorithms rank subsets of features. Unlike feature evaluation algorithms, however, a subset selection algorithm suitable for the present embodiments aims at selecting the subset of features with the highest impact on the response of the subject under analysis to the selected food, while accounting for the degree of redundancy between the features included in the subset. The benefits from feature subset selection include facilitating data visualization and understanding, reducing measurement and storage requirements, reducing training and utilization times, and eliminating distracting features to improve classification.

Two basic approaches to subset selection algorithms are the process of adding features to a working subset (forward selection) and deleting from the current subset of features (backward elimination). In machine learning, forward selection is done differently than the statistical procedure with the same name. The feature to be added to the current subset in machine learning is found by evaluating the performance of the current subset augmented by one new feature using cross-validation. In forward selection, subsets are built up by adding each remaining feature in turn to the current subset while evaluating the expected performance of each new subset using cross-validation. The feature that leads to the best performance when added to the current subset is retained and the process continues. The search ends when none of the remaining available features improves the predictive ability of the current subset. This process finds a local optimum set of features.

Backward elimination is implemented in a similar fashion. With backward elimination, the search ends when further reduction in the feature set does not improve the predictive ability of the subset. The present embodiments contemplate search algorithms that search forward, backward or in both directions. Representative examples of search algorithms suitable for the present embodiments include, without limitation, exhaustive search, greedy hill-climbing, random perturbations of subsets, wrapper algorithms, probabilistic race search, schemata search, rank race search, and Bayesian classifier.

A decision tree is a decision support algorithm that forms a logical pathway of steps involved in considering the input to make a decision.

The term "decision tree" refers to any type of tree-based learning algorithms, including, but not limited to, model trees, classification trees, and regression trees.

A decision tree can be used to classify the databases or their relation hierarchically. The decision tree has tree structure that includes branch nodes and leaf nodes. Each branch node specifies an attribute (splitting attribute) and a test (splitting test) to be carried out on the value of the splitting attribute, and branches out to other nodes for all possible outcomes of the splitting test. The branch node that is the root of the decision tree is called the root node. Each leaf node can represent a classification (e.g., whether a particular portion of the group database matches a particular portion of the subject-specific database) or a value (e.g., a predicted response of the subject under analysis to the selected food). The leaf nodes can also contain additional information about the represented classification such as a confidence score that measures a confidence in the represented classification (i.e., the likelihood of the classification being accurate). For example, the confidence score can be a continuous value ranging from 0 to 1, which a score of 0 indicating a very low confidence (e.g., the indication value of the represented classification is very low) and a score of 1 indicating a very high confidence (e.g., the represented classification is almost certainly accurate). The response of the subject to the selected food can be classified by traversing down the decision tree based on outcomes of the splitting tests of the branch nodes on the path until a leaf node is reached, which provides the response of the subject to the selected food.

Support vector machines are algorithms that are based on statistical learning theory. A support vector machine (SVM) according to some embodiments of the present invention can be used for classification purposes and/or for numeric prediction. A support vector machine for classification is referred to herein as "support vector classifier," support vector machine for numeric prediction is referred to herein as "support vector regression".

An SVM is typically characterized by a kernel function, the selection of which determines whether the resulting SVM provides classification, regression or other functions. Through application of the kernel function, the SVM maps input vectors into high dimensional feature space, in which a decision hyper-surface (also known as a separator) can be constructed to provide classification, regression or other decision functions. In the simplest case, the surface is a hyper-plane (also known as linear separator), but more complex separators are also contemplated and can be applied using kernel functions. The data points that define the hyper-surface are referred to as support vectors.

The support vector classifier selects a separator where the distance of the separator from the closest data points is as large as possible, thereby separating feature vector points associated with objects in a given class from feature vector points associated with objects outside the class. For support vector regression, a high-dimensional tube with a radius of acceptable error is constructed which minimizes the error of the data set while also maximizing the flatness of the associated curve or function. In other words, the tube is an envelope around the fit curve, defined by a collection of data points nearest the curve or surface.

An advantage of a support vector machine is that once the support vectors have been identified, the remaining observations can be removed from the calculations, thus greatly reducing the computational complexity of the problem. An SVM typically operates in two phases: a training phase and a testing phase. During the training phase, a set of support vectors is generated for use in executing the decision rule. During the testing phase, decisions are made using the decision rule. A support vector algorithm is a method for training an SVM. By execution of the algorithm, a training set of parameters is generated, including the support vectors that characterize the SVM. A representative example of a support vector algorithm suitable for the present embodiments includes, without limitation, sequential minimal optimization.

The Least Absolute Shrinkage and Selection Operator (LASSO) algorithm is a shrinkage and/or selection algorithm for linear regression. The LASSO algorithm may minimizes the usual sum of squared errors, with a regularization, that can be an L1 norm regularization (a bound on the sum of the absolute values of the coefficients), an L2 norm regularization (a bound on the sum of squares of the coefficients), and the like. The LASSO algorithm may be associated with soft-thresholding of wavelet coefficients, forward stagewise regression, and boosting methods. The LASSO algorithm is described in the paper: Tibshirani, R, Regression Shrinkage and Selection via the Lasso, J. Royal. Statist. Soc B., Vol. 58, No. 1, 1996, pages 267-288, the disclosure of which is incorporated herein by reference.

A Bayesian network is a model that represents variables and conditional interdependencies between variables. In a Bayesian network variables are represented as nodes, and nodes may be connected to one another by one or more links. A link indicates a relationship between two nodes. Nodes typically have corresponding conditional probability tables that are used to determine the probability of a state of a node given the state of other nodes to which the node is connected. In some embodiments, a Bayes optimal classifier algorithm is employed to apply the maximum a posteriori hypothesis to a new record in order to predict the probability of its classification, as well as to calculate the probabilities from each of the other hypotheses obtained from a training set and to use these probabilities as weighting factors for future predictions of the response to food. An algorithm suitable for a search for the best Bayesian network, includes, without limitation, global score metric-based algorithm. In an alternative approach to building the network, Markov blanket can be employed. The Markov blanket isolates a node from being affected by any node outside its boundary, which is composed of the node's parents, its children, and the parents of its children.

Instance-based algorithms generate a new model for each instance, instead of basing predictions on trees or networks generated (once) from a training set.

The term "instance", in the context of machine learning, refers to an example from a database.

Instance-based algorithms typically store the entire database in memory and build a model from a set of records similar to those being tested. This similarity can be evaluated, for example, through nearest-neighbor or locally weighted methods, e.g., using Euclidian distances. Once a set of records is selected, the final model may be built using several different algorithms, such as the naive Bayes.

From 13 the method may loop back to 12 wherein the sampling rate is varied based on the calculated patterns. For example, when a sleep pattern is calculated and the method determines, based on that pattern, that the subject is sleeping, the sampling rate can be reduced, and when a social interaction pattern is calculated and the method determines, based on that pattern, that the subject experience extensive social interaction, the sampling rate can be increased.

The method optionally and preferably continues to 14 at which the behavioral pattern is compared with a reference behavioral pattern. The reference behavioral pattern can be subject-specific or non-subject-specific. A subject-specific reference behavioral pattern can be a history behavioral pattern calculated for the particular subject when the condition of the subject was known (for example, as a result of an in-person examination by a physician). A non-subject-specific reference behavioral pattern can be a behavioral pattern calculated based on behavioral parameters collected from multiple subjects that form a behavioral group, which may or may not include the subject under analysis. Each value of such non-subject-specific reference behavioral pattern can be calculated based on representative values of the behavioral parameters where the representative values can be obtained, for example, by applying an averaging procedure to the behavioral parameters collected from the group.

The method optionally and preferably continues to 15 at which the likelihood that the subject is experiencing or is expected to experience an abnormal condition is estimated based on the comparison. For example, when the reference behavioral pattern is a subject-specific reference behavioral pattern that is a history behavioral pattern calculated for the particular subject when the condition of the subject was abnormal, or when the reference behavioral pattern is a non-subject-specific reference behavioral pattern calculated based on behavioral parameters collected from multiple subjects that form a behavioral group identified as experiencing abnormal condition, the method can estimate that the likelihood is high if the method determines that the pattern calculated at 13 is similar to the reference pattern, and that the likelihood is low if the method determines that the pattern calculated at 13 is not similar to the reference pattern.

Conversely, when the reference behavioral pattern is a subject-specific reference behavioral pattern that is a history behavioral pattern calculated for the particular subject when the condition of the subject was normal, or when the reference behavioral pattern is a non-subject-specific reference behavioral pattern calculated based on behavioral parameters collected from multiple subjects that form a behavioral group identified as experiencing normal condition, method can estimate that the likelihood is low if the pattern calculated at 13 is similar to the reference pattern, and that the likelihood is high if the pattern calculated at 13 is not similar to the reference pattern.

The similarity between patterns can be expressed in a binary manner (e.g., similar or not similar) or, more preferably, a level of similarity can be calculated by defining the distance (e.g., the Euclidian distance, Chebyshev distance, etc) between the patterns within the multidimensional space spanned by the behavioral parameters.

The abnormal condition can correspond to an episode of a mental and/or behavioral disorder, such as, but not limited to, depression and major depressive disorder, obsessive compulsive disorder, schizophrenia, visual and auditory hallucinations, anxiety disorder, and bipolar disorder (manic depressive illness). The abnormal condition can correspond to an episode selected from the group consisting of major depressive episode, manic episode, mixed episode and hypomanic episode.

The abnormal condition can correspond to Schizophrenia including the subtypes Paranoid Type, Disorganised Type, Catatonic Type, Undifferentiated Type and Residual Type; Schizophreniform Disorder; Schizoaffective Disorder including the subtypes Bipolar Type and Depressive Type; Delusional Disorder including the subtypes Erotomanic Type, Grandiose Type, Jealous Type, Persecutory Type, Somatic Type, Mixed Type and Unspecified Type; Brief Psychotic Disorder; Shared Psychotic Disorder; Psychotic Disorder Due to a General Medical Condition including the subtypes With Delusions and With Hallucinations; Substance-Induced Psychotic Disorder including the subtypes With Delusions and With Hallucinations; and Psychotic Disorder Not Otherwise Specified.

The abnormal condition can correspond to depression and mood disorders including Major Depressive Episode, Manic Episode, Mixed Episode and Hypomanic Episode; Depressive Disorders including Major Depressive Disorder, Dysthymic Disorder, Depressive Disorder Not Otherwise Specified (311); Bipolar Disorders including Bipolar I Disorder, Bipolar II Disorder (Recurrent Major Depressive Episodes with Hypomanic Episodes), Cyclothymic Disorder and Bipolar Disorder Not Otherwise Specified; Other Mood Disorders including Mood Disorder Due to a General Medical Condition which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified.

The abnormal condition can correspond to anxiety disorders including Panic Attack; Panic Disorder including Panic Disorder without Agoraphobia and Panic Disorder with Agoraphobia; Agoraphobia; Agoraphobia Without History of Panic Disorder, Specific Phobia (formerly Simple Phobia) including the subtypes Animal Type, Natural Environment Type, Blood-Injection-Injury Type, Situational Type and Other Type), Social Phobia (Social Anxiety Disorder), Obsessive-Compulsive Disorder, Posttraumatic Stress Disorder, Acute Stress Disorder, Generalized Anxiety Disorder, Anxiety Disorder Due to a General Medical Condition, Substance-Induced Anxiety Disorder, Separation Anxiety Disorder, Adjustment Disorders with Anxiety and Anxiety Disorder Not Otherwise Specified.

The abnormal condition can correspond to a substance-related disorder including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence, Alcohol Abuse, Alcohol Intoxication, Alcohol Withdrawal, Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified; Amphetamine (or Amphetamine-Like)-Related Disorders such as Amphetamine Dependence, Amphetamine Abuse, Amphetamine Intoxication, Amphetamine Withdrawal, Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified; Caffeine Related Disorders such as Caffeine Intoxication, Caffeine-Induced Anxiety Disorder, Caffeine-Induced Sleep Disorder and Caffeine-Related Disorder Not Otherwise Specified; *Cannabis*-Related Disorders such as *Cannabis* Dependence, *Cannabis* Abuse, *Cannabis* Intoxication, *Cannabis* Intoxication Delirium, *Cannabis*-Induced Psychotic Disorder, *Cannabis*-Induced Anxiety Disorder and *Cannabis*-Related Disorder Not Otherwise Specified; Cocaine-Related Disorders such as Cocaine Dependence, Cocaine Abuse, Cocaine Intoxication, Cocaine Withdrawal, Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified; Hallucinogen-Related Disorders such as Hallucinogen Dependence, Hallucinogen Abuse, Hallucinogen Intoxication, Hallucinogen Persisting Perception Disorder (Flashbacks), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified; Inhalant-Related Disorders such as Inhalant Dependence, Inhalant Abuse, Inhalant Intoxication, Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified; Nicotine-Related Disorders such as Nicotine Dependence, Nicotine Withdrawal and Nicotine-Related Disorder Not Otherwise Specified; Opioid-Related Disorders such as Opioid Dependence, Opioid Abuse, Opioid Intoxication, Opioid Withdrawal, Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified; Phencyclidine (or Phencyclidine-Like)-Related Disorders such as Phencyclidine Dependence, Phencyclidine Abuse, Phencyclidine Intoxication, Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified; Sedative-, Hypnotic-, or Anxiolytic-Related Disorders such as Sedative, Hypnotic, or Anxiolytic Dependence, Sedative, Hypnotic, or Anxiolytic Abuse, Sedative, Hypnotic, or Anxiolytic Intoxication, Sedative, Hypnotic, or Anxiolytic Withdrawal, Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified; Polysubstance-Related Disorder such as Polysubstance Dependence; and Other (or Unknown) Substance-Related Disorders such as Anabolic Steroids, Nitrate Inhalants and Nitrous Oxide.

The abnormal condition can correspond to a sleep disorder including primary sleep disorders such as Dyssomnias such as Primary Insomnia, Primary Hypersomnia, Narcolepsy (347), Breathing-Related Sleep Disorders, Circadian Rhythm Sleep Disorder and Dyssomnia Not Otherwise Specified; primary sleep disorders such as Parasomnias such as Nightmare Disorder, Sleep Terror Disorder, Sleepwalking Disorder and Parasomnia Not Otherwise Specified; Sleep Disorders Related to Another Mental Disorder such as Insomnia Related to Another Mental Disorder and Hypersomnia Related to Another Mental Disorder; Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome.

The abnormal condition can correspond to an eating disorders such as Anorexia Nervosa including the subtypes Restricting Type and Binge-Eating/Purging Type; Bulimia Nervosa including the subtypes Purging Type and Nonpurging Type; Obesity; Compulsive Eating Disorder; Binge Eating Disorder; and Eating Disorder Not Otherwise Specified.

The abnormal condition can correspond to attention-deficit/hyperactivity disorder including the subtypes Attention-Deficit/Hyperactivity Disorder Combined Type, Attention-Deficit/Hyperactivity Disorder Predominantly Inattentive Type, Attention-Deficit/Hyperactivity Disorder Hyperactive-Impulse Type and Attention-Deficit/Hyperactivity Disorder Not Otherwise Specified; Hyperkinetic Disorder; Disruptive Behaviour Disorders such as Conduct Disorder including the subtypes childhood-onset type, Adolescent-Onset Type and Unspecified Onset, Oppositional Defiant Disorder and Disruptive Behaviour Disorder Not Otherwise Specified; and Tic Disorders such as Tourette's Disorder.

The abnormal condition can correspond to personality disorder including the subtypes Paranoid Personality Disorder, Schizoid Personality Disorder, Schizotypal Personality Disorder, Antisocial Personality Disorder, Borderline Personality Disorder, Histrionic Personality Disorder, Narcissistic Personality Disorder, Avoidant Personality Disorder, Dependent Personality Disorder, Obsessive-Compulsive Personality Disorder and Personality Disorder Not Otherwise Specified;

The abnormal condition can correspond to dissociative identity disorder. The abnormal condition can correspond to addiction.

The abnormal condition can correspond to a non-mental disorder, particularly a physiological disorder that affects behavior and locomotion, e.g., a disorder that is characterized by a relapsing-remitting pattern. Representative examples include, without limitation, autoimmune diseases, recurring infectious diseases, etc.

From 15 the method may loop back to 12 wherein the sampling rate is varied based on the calculated patterns. For example, when the method estimates a high likelihood that the subject is experiencing or is expected to experience an abnormal condition, the method can increase the sampling rate, and when the method estimates a low likelihood that the subject is experiencing or is expected to experience an abnormal condition, the method can decrease the sampling rate.

The method ends at 16.

Figure 2:
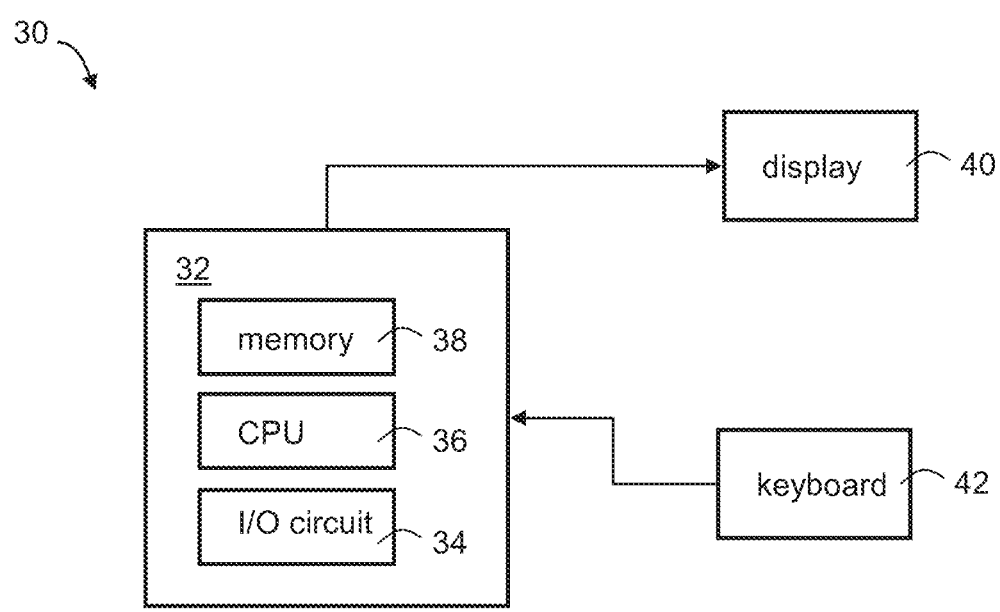

FIG. 2 is a schematic illustration of a data processing system 30 according to some embodiments of the present invention. System 30 comprises a computer 32, which typically comprises an input/output (I/O) circuit 34, a data processor, such as a central processing unit (CPU) 36 (e.g., a microprocessor), and a memory 46 which typically includes both volatile memory and non-volatile memory. I/O circuit 34 is used to communicate information in appropriately structured form to and from other CPU 36 and other devices or networks external to system 30. CPU 36 is in communication with I/O circuit 34 and memory 38. These elements can be those typically found in most general purpose computers and are known per se.

A display device 40 is shown in communication with data processor 32, typically via I/O circuit 34. Data processor 32 issued to display device 40 graphical and/or textual output images generated by CPU 36. A keyboard 42 is also shown in communication with data processor 32, typically I/O circuit 34.

It will be appreciated by one of ordinary skill in the art that system 30 can be part of a larger system. For example, system 30 can also be in communication with a network, such as connected to a local area network (LAN), the Internet or a cloud computing resource of a cloud computing facility.

In some embodiments of the invention data processor 32 of system 30 is configured for receiving from a mobile device of the subject sensor data and/or device state data; remotely controlling the mobile device so as to vary a sampling rate of sensors of the mobile device; analyzing the data to provide one or more behavioral patterns associated with the subject; accessing memory 38 and/or I/O circuit to obtain a reference behavioral pattern; comparing the behavioral pattern with a reference behavioral pattern, and estimating the likelihood that the subject is experiencing or is expected to experience an abnormal condition based on the comparison, as further detailed hereinabove. The data processor 32 can display the estimated likelihood on display 42 and/or record the estimated likelihood on a non-volatile computer readable medium.

In some embodiments of the invention system 30 communicates with a cloud computing resource (not shown) of a cloud computing facility, wherein the cloud computing resource is configured for receiving from a mobile device of the subject sensor data and/or device state data; remotely controlling the mobile device so as to vary a sampling rate of sensors of the mobile device; analyzing the data to provide one or more behavioral patterns associated with the subject; accessing a memory to obtain a reference behavioral pattern; comparing the behavioral pattern with a reference behavioral pattern, and estimating the likelihood that the subject is experiencing or is expected to experience an abnormal condition based on the comparison, as further detailed hereinabove. The cloud computing resource can display the estimated likelihood on a display and/or record the estimated likelihood on a non-volatile computer readable medium.

The method as described above can be implemented in computer software executed by system 30. For example, the software can be stored in of loaded to memory 38 and executed on CPU 36. Thus, some embodiments of the present invention comprise a computer software product which comprises a computer-readable medium, more preferably a non-transitory computer-readable medium, in which program instructions are stored. The instructions, when read by data processor 32, cause data processor 32 to receive from a mobile device of the subject sensor data and/or device state data and execute the method as described above.

Alternatively, the computation capabilities of system 30 can be provided by dedicated circuitry. For example, CPU 30 and/or memory 46 can be integrated into dedicated circuitry configured for receiving from a mobile device of the subject sensor data and/or device state data; remotely controlling the mobile device so as to vary a sampling rate of sensors of the mobile device; analyzing the data to provide one or more behavioral patterns associated with the subject; accessing a memory to obtain a reference behavioral pattern; comparing the behavioral pattern with a reference behavioral pattern, and estimating the likelihood that the subject is experiencing or is expected to experience an abnormal condition based on the comparison, as further detailed hereinabove. The dedicated circuitry can display the estimated likelihood on a display and/or record the estimated likelihood on a non-volatile computer readable medium.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Relapsing-remitting mental illnesses lead to significant psychological, functional and occupational impairment of those whom they affect. Episodes related to these illnesses may have devastating effects, may lead to prolonged hospitalization and in some cases can be life threatening. Notable examples for such illnesses are mental disorders with recurring episodes, e.g. bipolar disorder (estimated prevalence of 4%), schizophrenia (prevalence of 0.3-0.7%), and clinical depression (estimated prevalence of 4.3%). According to the World Health Organization (WHO) mental illnesses lead to the heaviest social and economic burden on societies, beyond that of cancer or of cardiovascular diseases.

Preventive medicine may reduce illness severity (or stop its outburst altogether) and significantly minimize recovery time and healthcare costs. It may be done by identifying the symptoms and treating the illness before a severe psychiatric episode breaks. For example, Bipolar Disorder is a severe chronic form of mental illness associated with recurrent episodes of mania and depression. The early detection of the onset of a manic episode was shown to be feasible and effective, thus efficient monitoring of the bipolar individual is a welcome addition to the clinical arsenal.

Smartphone technology and specifically the embedded sensors in smartphones have significantly advanced in the last seven years. These sensors can record multiple parameters that may give insight about the user's daily routine and physiology. Such parameters include, for example: mobility and location (using the accelerometer and GPS sensors), social interactions (using the SMS and Call logs) or vocal characteristics. Data acquired from smartphones can be analyzed using classification and machine-learning algorithms to identify patterns of a user's behavior and detect deviations from these patterns. These technologies are integrated to create a platform that monitors the health of subjects that are susceptible to the recurrence of an episode of a severe illness.

Continuously recording data from the user's smartphone sensors according to some embodiments of the present invention allows efficient and non-invasive monitoring of the user's mental health state. Effective preventive medicine can be achieved with small financial investment and high user transparency.

Figure 3:
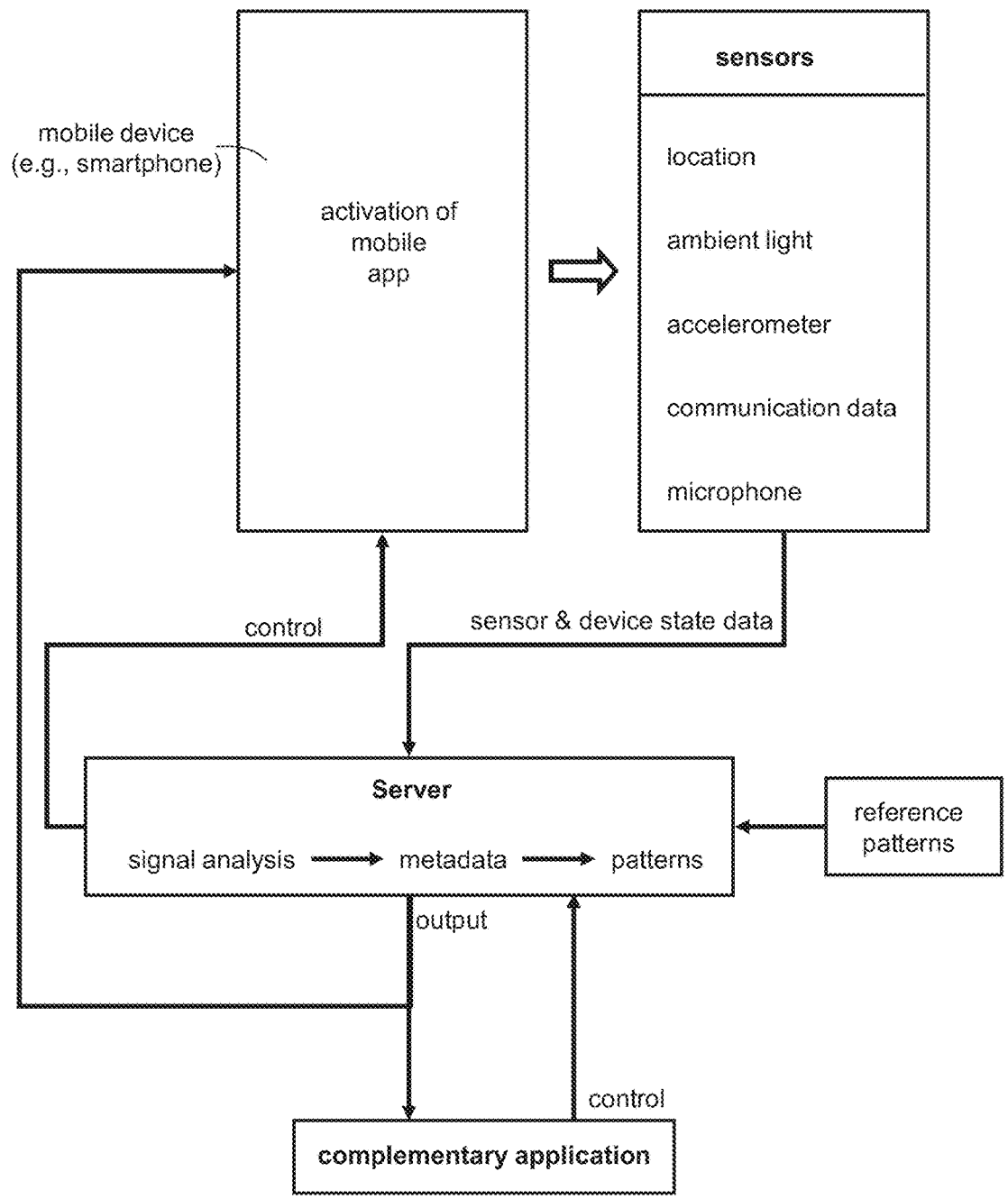

FIG. 3 shows an overview of a deployed system which can be used according to some embodiments of the present invention. Upon activation of a mobile app in the user's mobile device (e.g., smartphone), sensor data and device state data are collected by the mobile app and transmitted, optionally and preferably in a compressed form, to a remote server. The server analyses the signals to provide metadata and then analyses the metadata to provide patterns. The server can output information (e.g., alerts, analysis results, likelihoods, etc) as a feedback to the mobile device of the subject, and/or to a remote data processor, running a complementary application. The remoter data processor can be operated or viewed by a medical practitioner (e.g., a physician) or an otherwise authorized individual (e.g., a family member). The server can transmits control signals to the mobile device, and the complementary application can instruct the remote data processor to transmit control signal to the server.

The server can be a central data processor that receives data from multiple mobile devices of multiple subjects. The mobile device can comprise at least one, more preferably multiple, sensors, as well as hardware and software for acquisition, computation and communication.

The mobile device preferably includes a variety of optional hardware and software components. In general, a component in the mobile device can communicate with any other component of the device, although not all connections are shown for ease of illustration. The mobile device can be any of a variety of computing devices (e.g., cell phone, smartphone, handheld computer, laptop computer, notebook computer, tablet device, notebook, media player, Personal Digital Assistant (PDA), camera, video camera, or the like). In various exemplary embodiments of the invention the mobile device is a smart phone.

The mobile device can allow wireless two-way communications with one or more mobile communications networks, such as a Wi-Fi, cellular, or satellite network.

The mobile device optionally and preferably comprises a controller or processor (e.g., a signal processor, microprocessor, ASIC, or other control and processing logic circuitry) for performing such tasks as signal coding, data processing, input/output processing, power control, and/or other functions. An operating system can control the allocation and usage of the components and support for one or more application programs, such as a visual recognition and tracking application that implements one or more of the innovative features described herein. The application programs can include at least one of visual recognition software, tracking software, and common mobile computing applications (e.g., telephony applications, email applications, calendars, contact managers, web browsers, messaging applications) or any other computing application.

The mobile device can include memory. The memory can include non-removable memory and/or removable memory. The non-removable memory can include RAM, ROM, flash memory, a hard disk, or other well-known memory storage technologies. The removable memory can include flash memory or a Subscriber Identity Module (SIM) card, which is well known in Global System for Mobile Communications (GSM) communication systems, or other well-known memory storage technologies, such as "smart cards." The memory can be used for storing data and/or code for running the operating system and the applications. Example data can include web pages, text, images, sound files, image data, video data, or other data sets to be sent to and/or received from one or more network servers or other devices via one or more wired or wireless networks. The memory can be used to store a subscriber identifier, such as an International Mobile Subscriber Identity (IMSI), and an equipment identifier, such as an International Mobile Equipment Identifier (IMEI). Such identifiers can be transmitted to a network server to identify users and equipment.

The mobile device can support one or more input devices, such as a touchscreen (e.g., capable of capturing finger tap inputs, finger gesture inputs, multi-finger tap inputs, multi-finger gesture inputs, or keystroke inputs from a virtual keyboard or keypad), microphone (e.g., capable of capturing voice input), camera (e.g., capable of capturing still picture images and/or video images), physical keyboard, buttons and/or trackball and one or more output devices, such as a speaker and a display. Other possible output devices can include piezoelectric or other haptic output devices. Some devices can serve more than one input/output function. For example, a touchscreen and a display can be combined into a single input/output device.

A wireless modem can be coupled to one or more antennas (not shown) and can support two-way communications between the processor of the mobile device and external devices, as is well understood in the art. The modem is shown generically and can include, for example, a cellular modem for communicating at long range with the mobile communication network, a Bluetooth-compatible modem, or a Wi-Fi-compatible modem for communicating at short range with an external Bluetooth-equipped device or a local wireless data network or router. The wireless modem is typically configured for communication with one or more cellular networks, such as a GSM network for data and voice communications within a single cellular network, between cellular networks, or between the mobile device and a public switched telephone network (PSTN).

The mobile device can further include at least one input/output port, a power supply, a satellite navigation system receiver, such as a Global Positioning System (GPS) receiver, sensors, such as, for example, an accelerometer, a gyroscope, a compass, or an infrared proximity sensor for detecting the orientation or motion of the device, a transceiver (for wirelessly transmitting analog or digital signals) and/or a physical connector, which can be a USB port, IEEE 1394 (FireWire) port, and/or RS-232 port. The above components are not required or all-inclusive, as any of the above components can be deleted and other components can be added.

The mobile device can determine location data that indicates the location of the mobile device based upon information received through the satellite navigation system receiver (e.g., GPS receiver). Alternatively, the mobile device can determine location data that indicates the location of the mobile device in another way. For example, the location of the mobile device can be determined by triangulation between cell towers of a cellular network. Or, the location of the mobile device can be determined based upon the known locations of Wi-Fi routers in the vicinity of the mobile device. The location data can be updated every second or on some other basis, depending on implementation and/or user settings. Regardless of the source of location data, the mobile device can provide the location data to a map navigation tool for use in map navigation. For example, the map navigation tool periodically requests, or polls for, current location data through an interface exposed by the operating system (which in turn can get updated location data from another component of the mobile device), or the operating system pushes updated location data through a callback mechanism to any application (such as the visual recognition and tracking application described herein) that has registered for such updates.

With the visual recognition and tracking application and/or other software or hardware components, the mobile device can implement the technologies described herein. For example, the processor can update a scene and/or list, view, or track objects in real time. As a client computing device, the mobile device can send requests to a server computing device, and receive images, object data, or other data in return from the server computing device.

For example, the mobile device can be a tablet device, a personal assistance device. The mobile device can be handheld, carried by, wearable by or mountable on the subject.

Many types of sensor data and device state data can be collected by the mobile app. For example, location sensors can provide longitude, latitude and/or height (e.g., ellipsoidal height), ambient light sensor(s) can provide illumination level (e.g., Lux), accelerometer sensor(s) can provide accelerometric and/or gravitational data, communication sensors and communication apps can provide text message and call data (both native apps data and add-on apps, such as WhatsApp®, data), the microphone(s) can provide audio data, which can be characterized by the mobile device or by the server, according to average amplitude, dominant frequency and/or spectral flatness. The data is transmitted by mobile device as signals. Preferably, the mobile device provides signals pertaining to at least one or at least two or at least three or at least four or at least five or at least six or at least seven or at least eight or at least nine or at least ten, e.g., each of the following types of information:

Audio
Location (based on a GPS, cellular-network localization, or based on another method for localization or tracking)
Acceleration
Luminosity (by a light sensor)
Communication activity log (calls and text messages)
Number of contacts
Turning the screen on/off
Turning the device on/off
Plugged/unplugged from a charger
Amount of acquired data
Amount and identity of running applications
Physical interaction with touchscreen
Keyboard usage The server receives the signals from the mobile device, and automatically applies signal analysis to the signals such as to estimate one or more, more preferably multiple quantified behavioral parameters, thereby forming metadata. The metadata is then further processed by the server to extract behavioral patterns that describe the subject's routine and physiology over a predetermined time period (for example, the behavioral patterns that describe the subject's daily routine and physiology). Representative examples of behavioral patterns extractable by the data processor include, without limitation:

Estimated sleep and activity patterns—indicating sleeping habits (duration, offset) and activity analysis
Communication patterns—indicating social interactions
Locations patterns—indicating motion in space
Speech patterns—indicating vocal characteristics
Mobile device use patterns—usage of applications and using the Internet.

Figure 4:
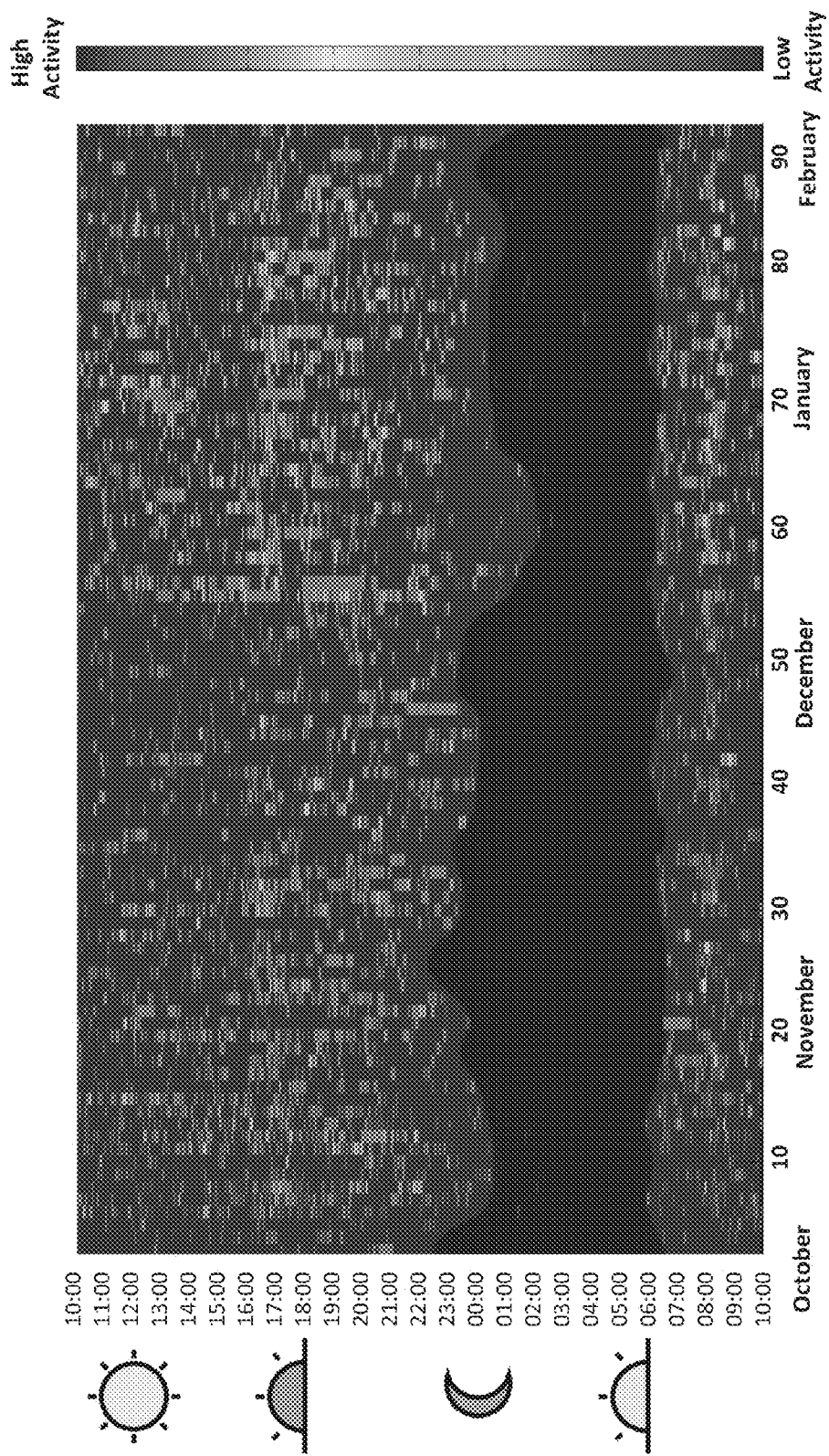

For example, displaying sensory data as a 2D sonogram can highlight sleep patterns, from which the relatively accurate sleep and activity times can be extracted. FIG. 4 is a sonogram that has been obtained according to some embodiments of the present invention. The sonogram displays the sleep and activity routine of a human subject for the course of three and a half months. The sonogram displays the activity with a continuous scale using a color code shown on the right hand side of FIG. 4. The activity is extracted from all sensors and an estimated pattern of the estimated sleep period is marked in dark blue.

In some embodiments of the invention the server analyzes the data to extract a physical activeness parameter. This can be done by employing a dynamic threshold on location based sensors, physical activity sensors, light, heart rate and voice.

In some embodiments of the invention the server identifies periodic movements such as shaking.

In some embodiments of the invention the server employs classification procedures based on the voice signal for identifying segments of speech. The identified segments can be used to extract parameters that characterize a specific mood or condition. Representative example of such parameters including, without limitation, average amplitude of voice, average frequency of voice, and pressure of speech.

The estimated behavior parameter forms an estimated point in a multidimensional behavioral space. The behavior parameters are optionally and preferably tracked, continuously or intermittently, over time to provide a collection of points, each representing the estimated behavior at one time-interval. In various exemplary embodiments of the invention the collection of points over a predetermined time period (e.g., over one day) are analyzed so as to classify the points in the multidimensional space into one or more classification groups, each defining a behavioral routine of the subject. The classification optionally includes clustering. The analysis can optionally and preferably include use of a machine learning procedure.

In various exemplary embodiments of the invention the server compares the behavioral patterns to reference behavioral patterns that are optionally and preferably read from a computer readable medium. The server uses the comparison for estimating the likelihood that the subject is experiencing or is approaching an abnormal condition, and optionally and preferably outputs at least one of the behavioral patterns and/or the likelihood to a display.

The reference behavioral patterns can be obtained from a database of expected deviations in clinically pathological conditions. The reference behavioral patterns can alternatively or additionally be obtained from a subject-specific routine as learned by a machine learning procedure. The reference behavioral patterns can alternatively or additionally include history patterns that correspond to deviation (e.g., prodromes) specific to the subject under analysis or a group of subjects.

When the server identifies a deviation that is suspected as an approaching an episode of abnormal condition the server can generate an alert that can be transmitted as a feedback to the subject (e.g., to the mobile device) and/or to any other alert receiving device such as a display monitored by a care giver and/or a relative.

The analysis according to some embodiments of the present invention can optionally and preferably be based on reports filled by the subject, records of the subject history, such as social events, stressful periods, occurrences of troubling incidents (trauma, battle, physical and sexual assaults and abuse). The analysis according to some embodiments of the present invention can optionally and preferably be based on known future events such as prospected stressful periods in work, exams periods, expected births or incurable illnesses of related people, expected participation in combatant military activity, expected use of newly prescribed drugs. The analysis according to some embodiments of the present invention can be used to determine correlations in behavior in large populations for the purpose of detection of large scale epidemics and mood changes within groups (classes of students and workers).

In some embodiments of the invention the server employs a scoring procedure, optionally and preferably system based on machine learning, which defines a weighted score to the communication parameters (calls, texts, VOIP services, social networks, and social circles) for creating a relative communication space.

In some embodiments of the invention the server retrieves the distance travelled, mode of transportation and/or user's places of interest based on location data from GPS, wireless networks, cellular network based location and/or motion sensors.

Exemplary Smart Phone App Features (i) The app samples the data from the sensors periodically, for example
Audio—every conversation
Location—every 20 minutes
Acceleration—every 2 minutes
Luminosity—every 2 minutes
Communication activity log—every day
Amount of acquired data—every 3 seconds while the screen is on
Amount of running applications—every 3 seconds while the screen is on.

(ii) The app displays the subject information regarding his behavioral patterns and alerts or indicates when there are deviations, displays reminders for taking medications, personalized recommendations, general information about the subject's mental disorder.

(iii) The app presents daily questions regarding the subject's mental state and daily routine.

(iv) The app communicates with a complementary application operated or viewed by a physician, and the subject can report his mental state or life events.

(v) The app allows remote access to the physician (via the complementary application), for example, to change the sampling rate of different sensors or to change the daily questions for the subject.

(vi) The app finds the amount of spelling mistakes, corrections and typing rate in the general usage of the software keyboard by the subject.

(vii) The app collects frequency of usage of social applications, such as, but not limited to, Whatsapp®, Facebook®, Twitter®, Hangouts®, Viber®.

(viii) The app collects amount of information transferred using the social applications.

(ix) The app accesses the subject's calendar to collects documented life events.

(x) The app reports, for example, to the complementary application, if the subject has removed the application.

(xi) The app reports, for example, to the complementary application, on financial transactions.

Exemplary Server Features (i) The server finds thresholds of activity for linear acceleration and ambient light.

(ii) The server assigns weight to each sensor. Active sensors have a larger weight than passive sensors.

(iii) The server generates an activity sonogram—combining a plurality of sensors (summing their weights) to a map of total activity. The sonogram may be generated once a day and can encompass a 24 hr activity.

(iv) The server extracts activity parameters such as, but not limited to, bed time, wake time, interrupts at the sleeping period, amount of activity during day time, activity patterns at different times during a day.

(v) The server extracts mobility parameters, such as, but not limited to, total locations per day, unique locations (not visited with a predetermined time period), total distance, distance between unique locations per day. Quantification can be (a) spending at least T minutes at the same location (T can be, for example, about 20) and/or (b) at least X km between locations (X can be, for example, about 1).

(vi) The server extracts communication parameters, such as, but not limited to, number of outgoing and incoming calls, average calls duration, number of outgoing and incoming messages, number of unique contacts, ratio between outgoing and incoming communication.

(vii) The server extracts a behavioral parameter describing the response time to text messages and calls.

(viii) The server detects the type of motion (walking, driving, cycling).

(ix) The server distinguishes between normative and obsessive usage in the smartphone, based on the frequency of switching between applications, the frequency of opening and closing applications, the frequency of turning on and off the screen, and the volume of data usage.

(x) The server detects motor movements (hands and/or body movements), and classifies them according to strength, duration, etc.

(xi) The sever searches for deviations for one or more of the parameters from the subject baseline. The baseline is optionally and preferably defined individually for each subject, for example, during a period in which the subject was healthy.

(xii) The server issues alerts or provide indications to the subject, the physician or family.

Exemplary Features of the Complementary Application

The complementary application is executed by a remoter data operated or viewed by a medical practitioner (e.g., a physician) or an otherwise authorized individual (e.g., a family member).

The complementary application provides a summary of all the subjects over a predetermined time period (e.g., a week). Each behavioral parameter (e.g., activity, communication, mobility, vocal characteristics) is marked as normal, below normal or above normal, for example, with an appropriate color code. The complementary application can also provide a total score for each subject indicating the amount and optionally direction of deviation from normal.

The complementary application can also generate a graphical representation describing an overview of a longer time-period (e.g., few months), for a particular subject and/or a particular parameter.

The complementary application can also provide a more detailed view of a time period between two dates selected by the operator. Such a detailed view can include:

Activity sonogram—combination of all a plurality of sensors on one map.

Mobility—each place is displayed as a rectangle, an empty area indicates movement and the line type (continuous, dashed, etc.) between places indicates the distance between one place to another.

Communication—specifying calls duration, time and type, messages time and type.

Hovering above graphs can display the value.

The complementary application can allow removing or adding sensors dynamically from the activity sonogram.

The complementary application can allow linking and unlinking a particular subject from the complementary application.

The complementary application can allow flagging a subject as more important.

The complementary application can allow adding events manually, which events can then be presented together with calculated parameters and graphs. Representative examples of manually added events include, without limitation, meeting with the physician (including the contents of the meeting as provided by the physician), hospitalization, starting taking medication, or any event reported by the subject. The drug type and dosage can also be input and presented.

The complementary application can also provide a mode of operation which depends on the subject's condition. For example, different types of presentation of a subject diagnosed as having ADHD, and for a subject diagnosed as having a severe mental disorder. Typically, for a subject that is not diagnosed as having a severe mental disorder, it is sufficient to display the manner and frequency of using the smartphone, replacing between applications, response time for messages/calls, speed of movement, speech ratio during a conversation.

The complementary application can allow defining the baseline period of the subject.

The complementary application can display alerts from the server, and whether or not alerts the subject received.

The complementary application can allow the medical practitioner to communicate with the patient via the app, for example, using instant text messages.

Exemplary Analysis Procedures

Estimation of Sleep and Activity

This procedure extracts the user's general activity pattern with parameters regarding the user's estimated sleep and activity, for example, the estimated duration of the user's night sleep, bed time and wake time.

This procedure receives one or more, preferable all, of the following parameters per each epoch (e.g., a minute): Timestamp (e.g., in units of [unix time]), Acceleration (e.g., in units of $[m/s^2]$), Luminance (e.g., in units of [lux]), Charge on (e.g., a binary or Boolean parameter), Screen on (e.g., a binary or Boolean parameter), Txt type (e.g., a binary or Boolean parameter), On call in (e.g., a binary or Boolean parameter), On call out (e.g., a binary or Boolean parameter), Data usage (e.g., a binary or Boolean parameter).

Each parameter represents an activity during the specific minute. "ChargeOn" indicates the occurrence of charger plugged/unplugged activity, during the specific minute. "ScreenOn" indicates the occurrence of a screen on/off activity, during the specific minute. "txtType" indicates outgoing/incoming text messages during the minute. "DataUsage" indicates using the internet during the minute.

Processing

Thresholding the data to detect real activity per sensor, per day, with a minute resolution—for the acceleration and luminance thresholding optionally and preferably includes using k-means algorithm, for example, between 5% and 95% of the sensor's signal values.

(i) Defining weights for all sensors. Acceleration and luminance optionally and preferably get a predetermined and reduced weight (e.g., 20% of all other weights) because they depend on environmental factors and not just on the user's activity.

(ii) All activities are combined for achieving the user's overall activeness during the day in each minute. The activities consist of, for example: minutes during which a message was sent, minutes during which the user has talked, minutes during which the acceleration and luminance are above their thresholds, minutes during which the charge state or screen state experienced a change.

(iii) Deciding sleep or activity in each hour:
Summing the activity in each hour.
An hour is considered as active if there is, e.g., about 30% of the average activeness.

An hour is active if it was considered active in, e.g., more than 50% of all days.

(iv) Closing gaps between activity hours, where there is high probability that there is activity.

(v) Reducing the pattern in order to correspond more accurately to the activity. For example, increasing the sleep hours from the last minute awake to the first minute awake.

Communication

This procedure finds the communicational habits of the user. This procedure receives one or more, preferably all, of the following parameters per epoch (e.g., calendar day): Timestamp (e.g., in units of [unix time]), Total call duration (e.g., in units of [sec]), Number of outgoing calls out, Number of incoming calls, Number of missed calls, Number of calls to and/or from unique contacts, Number of outgoing text messages, Number of incoming text messages, Number of text messages to and/or from unique contacts.

Processing

The following parameters are optionally and preferably analyzed and achieved every day and at different hours during the day:
  i. Number of incoming and outgoing calls
  ii. Number of incoming and outgoing text messages
  iii. Number of outgoing messages to all destinations, excluding calls to the most frequent destination
  iv. Missed calls
  v. Total calls duration, incoming and outgoing calls duration
  vi. Unique calls contacts
  vii. Unique text messages contacts.
  In some embodiments of the present invention the communication data can be processed into combined parameters, e.g., overall communication volume (Outgoing+Incoming communication), normalized communication outgoing/incoming ratio (e.g., Outgoing−Incoming/Outgoing+Incoming).

Mobility

This procedure receives one or more, preferably the following parameters per epoch (e.g., 30 minutes) of each day: Timestamp (e.g., in units of [unix time]), latitude (e.g., in units of [deg]), longitude (e.g., in units of [deg]).

This procedure optionally and preferably calculates unique locations and the time duration spent in each unique location. A unique location is where the time spent in this location is larger than a predetermined time threshold (e.g., 30 minutes) and the distance between this location and the next is higher than a predetermined distance threshold (e.g., 1 Km).

Processing (i) Finding the time of the current and previous locations.
(ii) Calculating the elapsed time in minutes and distance between the current and previous locations.
(iii) If the current location is the same as the previous—add the elapsed time to the duration.
(iv) If the time spent in previous location is larger than 20 minutes and the distance is higher than 1 Km—the previous location is unique.
(v) Defining the way of transportation between every two locations by the time and distance passed between them.
(vi) Displaying the motion data as a 2D sonogram, where the x-axis is minutes and the y-axis is days.

Speech

This procedure expects an input with one or more, preferably all, of the following parameters per each epoch (e.g., 1 minute) of a conversation: Timestamp (e.g., in units of

[unix time]), amplitude (e.g., in units of [dB]), main frequency (e.g., in units of [Hz]), Spectral flatness (e.g., in arbitrary units).

This procedure optionally and preferably calculates the amplitude of voice, frequency of voice, and ratio of speech to non-speech of the subject for each phone conversation.

Processing
i. Collecting all relevant samples to each phone conversation.
ii. Performing classification to distinguish between temporal samples representing speech to samples representing non-speech (silence of subject during the call).
iii. Calculating amplitude of speech that was detected in samples classified as speech.
iv. Calculating main frequency of speech that was detected in samples classified as speech.
v. Calculating the ratio of speech to non-speech time for each conversation.

Experiments

Three Helsinki approved studies with Geha, Be'er ya'acov and Sha'ar Menashe mental health centers in Israel have been performed. The study goals were:

Correlate data collected from smartphone sensors to professional diagnosis previously diagnosed unipolar, bipolar and schizoaffective subjects for the detection of onset of manic or depressive episodes.

Assess the predictive ability of manic or depressive episodes based on data collected from smartphone sensors.

Correlate data collected from smartphone sensors and professional diagnosis to changes in drug treatment dosage in affective subjects.

About 60 volunteers (~40 subjects with mental disorders and 20 healthy volunteers) were recruited and a smartphone application was installed on their smartphones.

Results

The observed data demonstrated that the system optionally and preferably is sensitive to clinically significant changes in patient's behavioral and emotional condition.

FIGS. 5A-C present the averaged call duration, speech ratio and motion distance, respectively, of a unipolar subject while having a mild depression episode. Mild depression was reported from approximately the 50th day of monitoring (marked with an arrow) and onwards. As shown, the averaged call duration and speech ratio decreased during the depression, while no significant change in the motion distance was observed.

FIGS. 6A-B present activity parameter and No. of outgoing text messages of a bipolar subject with a manic deterioration who was hospitalized approximately at the 40th day of monitoring (marked with an arrow). The activity parameter contains a combination of the activity volume during the day and sleep interrupts during the night. As shown, the activity increased significantly about one month before hospitalization and again about two weeks before hospitalization. Further, about one week before hospitalization the number of outgoing text messages was increased by a factor of about 12.

The results shown in FIGS. 5A-C and 6A-B demonstrate that the system optionally and preferably is sensitive to mild as well as significant changes and is capable of predicting a mental episode.

What is claimed is:

1. A method of estimating likelihood that a subject is experiencing or is expected to experience an abnormal condition, the method comprising:

automatically receiving from a mobile device of the subject, over a communication network, sensor data and device state data selected from the group consisting of electronic communication log data, screen state data, power on/off data, and battery state data, and storing said sensor data and device state data in a computer readable memory;

analyzing said sensor data and device state data by a remote computer to provide at least one behavioral pattern associated with said subject, and storing said at least one behavioral pattern in said computer readable memory;

comparing said behavioral pattern with a reference behavioral pattern; and estimating the likelihood that said subject is experiencing or is expected to experience an abnormal condition based on said comparison, and transmitting over said communication network an alert pertaining to said estimated likelihood to said mobile device of the subject;

wherein said analyzing comprises (i) estimating sleep offset from motion sensors of said mobile device and/or from device state data of said mobile device, said sleep offset being defined as a time difference between two sleep onset times according to a local clock, and (ii) including said estimated sleep offset as a parameter for said behavioral pattern, and wherein said estimating said likelihood is based in part on said parameter; and wherein said estimating the likelihood that said subject is experiencing or is expected to experience an abnormal condition, comprises estimating the likelihood that said subject is experiencing or is expected to experience a manic episode.

2. The method according to claim 1, wherein said analyzing comprises determining level of physical activeness of said subject.

3. The method of claim 2, wherein said determining said level of activeness comprises measuring speed of movement of said subject.

4. The method of claim 2, wherein said sensor data comprise location data and/or acceleration data, and wherein said determining said level of activeness comprises identifying periodic movements of said subject, based on said location data and/or said acceleration data.

5. The method according to claim 1, wherein said sensor data comprises audio data, and wherein said analysis comprises identifying speech compression in said audio data.

6. The method according to claim 1, wherein said analyzing comprises estimating sleep duration.

7. The method according to claim 1, wherein said analyzing comprises identifying temporary awakening periods.

8. The method according to claim 1, wherein said analyzing comprises calculating a score pertaining to activity level of said subject over at least one communication network.

9. The method according to claim 1, wherein said analyzing comprises executing a voice analysis procedure.

10. The method according to claim 9, wherein said voice analysis procedure is executed to identify speech compression event.

11. The method according to claim 1, wherein said sensor data comprise at least two different types of data.

12. The method according to claim 1, wherein said sensor data comprise at least three different types of data.

13. The method according to claim 1, wherein said sensor data comprise at least four different types of data.

14. The method according to claim 1, wherein said sensor data comprise data selected from the group consisting of location data, acceleration data, orientation data, audio data, ambient illumination data.

15. The method according to claim 1, wherein said device state data comprise data selected from the group consisting of at least one of electronic communication log data and screen state data.

16. The method according to claim 1, wherein said analyzing comprises executing a machine learning procedure.

17. The method of claim 16, wherein said machine learning procedure comprises a supervised learning procedure.

18. The method according to claim 16, wherein said machine learning procedure comprises at least one procedure selected from the group consisting of clustering, support vector machine, linear modeling, k-nearest neighbors analysis, decision tree learning, ensemble learning procedure, neural networks, probabilistic model, graphical model, Bayesian network, and association rule learning.

19. The method of claim 1, wherein said mobile device comprises a touch screen, wherein said analysis comprises: (i) determining pressure applied by said subject to said touch screen, said determining said pressure comprising measuring an area of said touch screen touched by said subject, and (ii) including said determined pressure as a pressure parameter for said behavioral pattern, and wherein said estimating said likelihood is based in part on said pressure parameter.

20. The method according to claim 1, wherein said receiving said sensor data comprises remotely controlling said mobile device so as to vary a sampling rate of sensors of said mobile device.

21. A method of determining a mental condition of a subject, the method comprising:
automatically receiving from a mobile device of the subject, over a communication network, sensor data and device state data selected from the group consisting of electronic communication log data, screen state data, power on/off data, and battery state data, and storing said sensor data and device state data in a computer readable memory;
analyzing said sensor data and device state data by a remote computer to provide at least one behavioral pattern associated with said subject, and storing said at least one behavioral pattern in said computer readable memory;
comparing said behavioral pattern with a reference behavioral pattern;
determining a mental condition of the subject based on said comparison; and
over said communication network, transmitting to the mobile device of the subject an output indicative of said mental condition to be displayed by said mobile device;
wherein said analyzing comprises (i) estimating a sleep offset from motion sensors of said mobile device and/or from device state data of said mobile device, said sleep offset being defined as a time difference between two sleep onset times, and (ii) including said estimated sleep offset as a parameter for said behavioral pattern, and wherein said estimating said mental condition is based in part on said parameter; and
wherein said mental condition is a mood disorder or a mood change.

22. The method of claim 21, wherein said providing said output comprises displaying said mental condition on a display of said mobile device.

23. The method of claim 21, wherein said mood disorder is selected from the group consisting of Substance-Induced Mood Disorder, Alcohol-Induced Mood Disorder, Amphetamine-Induced Mood Disorder, Cocaine-Induced Mood Disorder, Hallucinogen-Induced Mood Disorder, Inhalant-Induced Mood Disorder, Opioid-Induced Mood Disorder, Phencyclidine-Induced Mood Disorder, and Sedative-, Hypnotic- or Anxiolytic-Induced Mood Disorder.

* * * * *